US00PP12216P2

(12) United States Plant Patent
Glicenstein

(10) Patent No.: US PP12,216 P2
(45) Date of Patent: Nov. 20, 2001

(54) CHRYSANTHEMUM PLANT NAMED 'YOCARRIE'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/478,448

(22) Filed: Jan. 6, 2000

(51) Int. Cl.[7] ..... A01H 5/00
(52) U.S. Cl. ..... Plt./289

(58) Field of Search ..... Plt./289, 287

*Primary Examiner*—Howard J. Locker
(74) *Attorney, Agent, or Firm*—C. A. Whealy

(57) ABSTRACT

A distinct cultivar of Chrysanthemum plant named 'Yocarrie', characterized by its uniformly mounded plant habit; freely branching, dense, full plants; uniform flowering; decorative-type inflorescences that are about 3.9 cm in diameter; attractive golden yellow ray florets that are red bronze when opening giving a bi-colored appearance to young inflorescences; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and hereinafter referred to by the cultivar name Yocarrie.

The new cultivar is a product of a planned breeding program conducted by the Inventor in Salinas, Calif. and Alva. Fla. The objective of the breeding program is to create new garden-type Chrysanthemum cultivars having inflorescences with desirable inflorescence forms, attractive floret colors and good garden performance.

The new cultivar originated from a cross made by the Inventor in Salinas, Calif., in November, 1993, of the *Dendranthema grandiflora* cultivar Peachy Lynn. disclosed in U.S. Pat. No. 8,892, as the female, or seed, parent with an unidentified proprietary seedling selection as the male, or pollen, parent.

The cultivar Yocarrie was discovered and selected by the Inventor as a flowering plant within the progeny of the stated cross in a controlled environment in Alva, Fla. in November, 1996. The selection of this plant was based on its desirable inflorescence form, attractive ray floret color and excellent garden performance.

Asexual reproduction of the new cultivar by terminal cuttings taken in a controlled environment in Alva, Fla. has shown that the unique features of this new Chrysanthemum are stable and reproduced true to type in successive generations.

SUMMARY OF THE INVENTION

The cultivar Yocarrie has not been observed under all possible environmental conditions. The phenotype may vary somewhat with variations in environment such as temperature, daylength and light intensity, without, however, any variance in genotype.

The following traits have been repeatedly observed and are determined to be unique characteristics of 'Yocarrie'. These characteristics in combination distinguish 'Yocarrie' as a new and distinct cultivar:

1. Uniformly mounded plant habit.
2. Freely branching, dense, full plants.
3. Uniform flowering.
4. Decorative-type inflorescences that are about 3.9 cm in diameter.
5. Attractive golden yellow ray florets that are red bronze when opening giving a bi-colored appearance to young inflorescences.
6. Numerous inflorescences per plant.
7. Excellent garden performance.

Compared to plants of the parent cultivar, Peachy Lynn, plants of the new Chrysanthemum are larger, more flexible and less susceptible to breakage, and differ in ray floret color.

The new Chrysanthemum is similar to the Chrysanthemum cultivar Ginger, disclosed in U.S. Plant Pat. No. 6,403. However in side-by-side comparisons under commercial practice, plants of the new Chrysanthemum differ from plants of the cultivar Ginger in the following characteristics:

1. Plants of the new Chrysanthemum are more compact than plants of the cultivar Ginger.
2. Plants of the new Chrysanthemum have smaller leaves than plants of the cultivar Ginger.
3. Plants of the new Chrysanthemum flower about three weeks later than plants of the cultivar Ginger under natural season conditions.
4. Ray floret color of the new Chrysanthemum is lighter than ray floret color of the cultivar Ginger; however the color contrast between the opening and the developed florets is more distinct on plants of the new Chrysanthemum compared to plants fo the cultivar Ginger.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which more accurately describe the actual colors of the new Chrysanthemum.

The photograph at the top of the sheet comprises a top perspective view of a typical flowering plant of 'Yocarrie'.

The photograph at the bottom of the sheet comprises a close-up view of typical inflorescences of the cultivar 'Yocarrie'.

DETAILED BOTANICAL DESCRIPTION

In the following description, color references are made to The Royal Horticultural Society Colour Chart except where general terms of ordinary dictionary significance are used. The following observations and measurements describe plants grown in Pendelton, S.C., under conditions which approximate those generally used in commercial garden Chrysanthemum production. One rooted cutting was planted in a 15-cm container on Jul. 26, 1999 and plants were grown under natural season conditions. Plants were not pinched, that is, the terminal apex was not removed to enhance branching. Measurements and numerical values represent averages for typical flowering plants.

Botanical classification: *Dendranthema grandiflora* cultivar Yocarrie.

Commercial classification: Decorative-type garden chrysanthemum.

Parentage:

*Female parent.*—*Dendranthema grandiflora* cultivar Peachy Lynn, disclosed in U.S. Plant Pat. No. 8,892.

*Male parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle; mounded plant form. Stems initially upright, then outwardly spreading giving a uniformly mounded appearance to the plant. Freely branching with lateral branches potentially developing at every node.

*Plant height.*—About 28 cm.

*Plant spread.*—About 40 cm.

*Stems.*—Texture: Pubescent. Color: 146A.

*Foliage description.*—Leaf arrangement: Alternate. Length: About 4.8 cm. Width: About 3.8 cm. Apex: Cuspidate. Base: Mostly truncate. Margin: Palmately lobed, sinuses parallel. Texture: Upper surface sparsely pubescent; lower surface moderately pubescent. Veins prominent on lower surface. Petiole length: About 1.3 cm. Petiole diameter: About 2.5 mm. Color: Young foliage upper surface: 147A. Young foliage lower surface: 147B. Mature foliage upper surface: 147A. Mature foliage lower surface: 147B. Venation upper surface: 147A. Venation lower surface: 147B.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About six inflorescences per lateral; about 216 inflorescences per plant.

*Flowering response.*—Under natural season conditions, plants flower in the autumn about 72 days after planting.

*Inflorescence bud.*—Height: About 5 mm. Diameter: About 7 mm. Color: Between 146A and 143A.

*Inflorescence size.*—Diameter: About 3.9 cm. Depth (height): About 1.4 cm. Diameter of disc: About 3.5 mm.

*Ray florets.*—Shape: Elongated oblong, concave. Length: About 1.75 cm. Width: About 5.5 mm. Apex: Pointed. Margin: Entire. Texture: Smooth, glabrous, satiny. Orientation: Initially upright, then perpendicular to the peduncle. Number of ray florets per inflorescence: About 136. Color: When opening, upper surface: Golden yellow, 12A. When opening, lower surface: Red bronze, close to 184A to 185A. Opened inflorescence, upper surface: Golden yellow, 12A to 9A; apices, red bronze, 184A to 185A. Opened inflorescence, lower surface: Yellow, close to 9C, with faint red bronze overtones, close to 185A.

*Disc florets.*—Shape: Tubular, apex dentate. Length: About 5 mm. Width, apex and base: About 1 mm. Number of disc florets per inflorescence: About 27. Color: Immature: 154A. Mature: Apex: 14A. Midsection: Light greenish white. Base: White.

*Peduncle.*—Aspect: Flexible, angled about 55° to the stem. Length: First peduncle: About 72 cm. Fourth peduncle: About 10.5 cm. Diameter: About 2 mm. Texture: Pubescent. Color: 146A.

*Reproduction organs.*—Androecium: Present on disc florets only. Anther color: 14A. Pollen: Moderate. Pollen color: 14A. Gynoecium: Present on both ray and disc florets.

*Seed.*—Seed production has not been observed.

Disease resistance: Plants of the new Chrysanthemum have not been shown to be resistant to pathogens common to Chrysanthemums.

It is claimed:

1. A new and distinct cultivar of Chrysanthemum plant named 'Yocarrie', as illustrated and described.

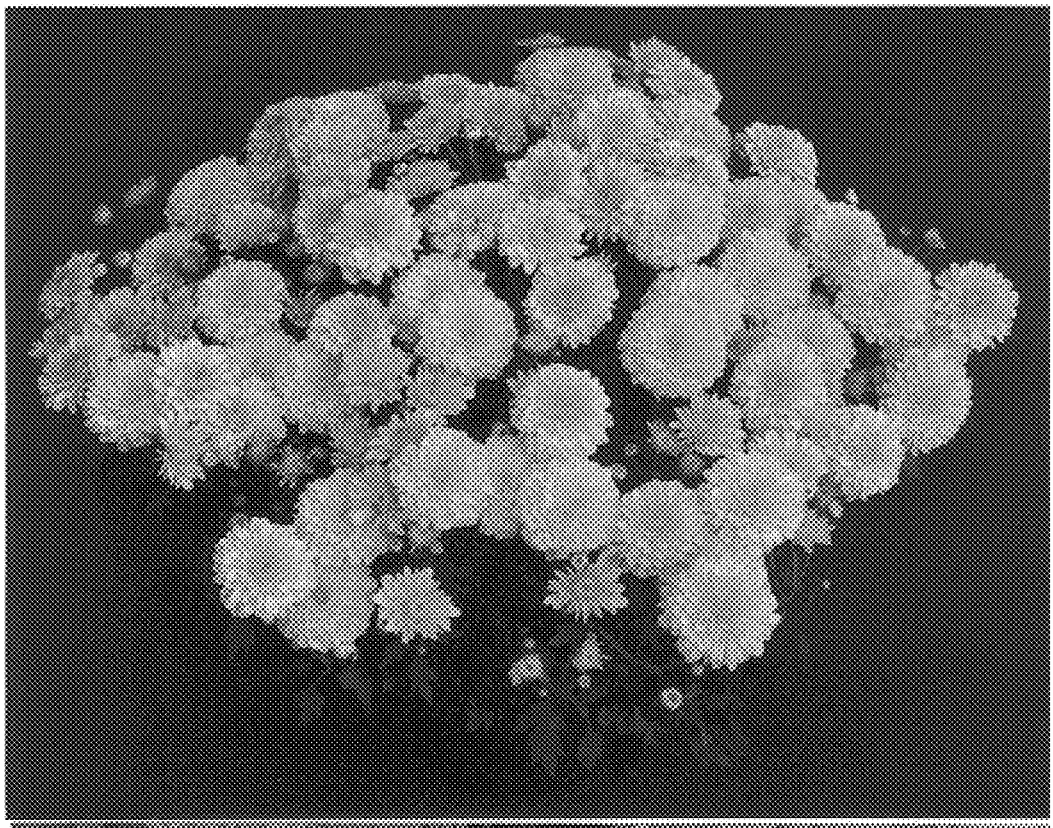
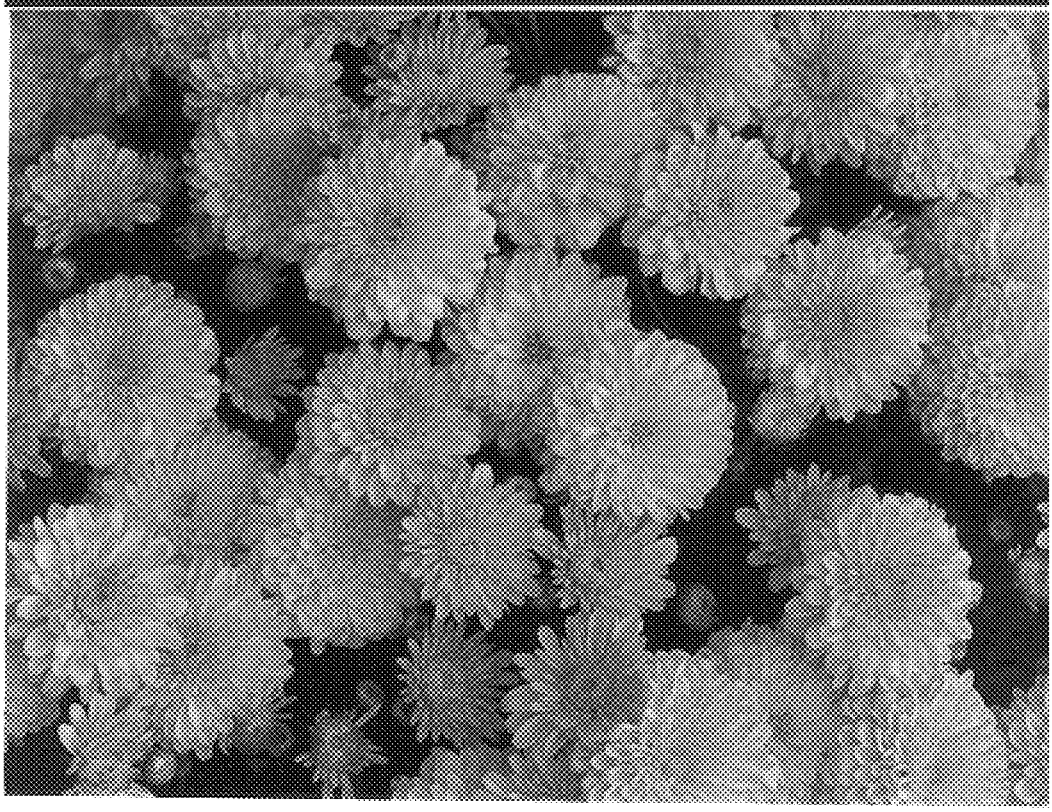

* * * * *